(12) United States Patent
Dusterhoft et al.

(10) Patent No.: US 12,193,715 B2
(45) Date of Patent: Jan. 14, 2025

(54) LATERAL ROD REDUCER

(71) Applicant: Astura Medical Inc., Iriving, TX (US)

(72) Inventors: Ross Dusterhoft, Irving, TX (US); Thomas Purcell, Irving, TX (US)

(73) Assignee: ASTURA MEDICAL INC, Irving, TX (US)

( * ) Notice: Subject to any disclaimer, the term of this patent is extended or adjusted under 35 U.S.C. 154(b) by 0 days.

(21) Appl. No.: 17/981,378

(22) Filed: Nov. 4, 2022

(65) Prior Publication Data
US 2023/0143005 A1   May 11, 2023

Related U.S. Application Data

(60) Provisional application No. 63/276,515, filed on Nov. 5, 2021.

(51) Int. Cl.
*A61F 2/44* (2006.01)
*A61B 17/70* (2006.01)

(52) U.S. Cl.
CPC .................. *A61B 17/7086* (2013.01)

(58) Field of Classification Search
None
See application file for complete search history.

(56) References Cited

U.S. PATENT DOCUMENTS

| | | | |
|---|---|---|---|
| 7,927,334 B2 * | 4/2011 | Miller ................ | A61B 17/7088 606/86 A |
| 2002/0095153 A1 * | 7/2002 | Jones ................ | A61B 17/7041 606/279 |
| 2003/0225408 A1 | 12/2003 | Nichols et al. | |
| 2006/0009775 A1 | 1/2006 | Dec et al. | |
| 2006/0089651 A1 | 4/2006 | Trudeau et al. | |
| 2006/0166535 A1 * | 7/2006 | Brumfield ................ | B25B 7/18 439/179 |
| 2007/0276379 A1 * | 11/2007 | Miller ................ | A61B 17/7088 606/86 A |
| 2009/0228054 A1 | 9/2009 | Hoffman et al. | |
| 2012/0191144 A1 | 7/2012 | Peultier et al. | |
| 2015/0157367 A1 * | 6/2015 | Biedermann ...... | A61B 17/7089 606/279 |

(Continued)

OTHER PUBLICATIONS

International Search Report and Written Opinion in PCT Application No. PCT/US22/49056 dated Mar. 31, 2023.

*Primary Examiner* — Jan Christopher L Merene
(74) *Attorney, Agent, or Firm* — Michael R. Shelin

(57) ABSTRACT

The present invention is directed to a rod reducer that is both a lateral rod reducer and an axial rod reducer that uses an entirely different mechanism never before used for lateral rod reduction. The lateral rod reducer is configured to move a spinal fixation rod that is not aligned with the pedicle screw to a position above the tulip slot or U-shaped channel. Once in position, the lateral rod reducer also provides an axial rod reducer to advance the spinal fixation rod axially into the tulip slot. Splitting the reducer body geometry to create a hinged jaw that is then driven by a linkage system is novel. The lateral rod reducer of the present invention allows for incremental lateral reduction that utilizes a threaded linkage feature for increased power/mechanical advantage when laterally reducing. This will allow for new techniques of lateral rod manipulation in deformity cases.

14 Claims, 6 Drawing Sheets

(56) References Cited

U.S. PATENT DOCUMENTS

| | | | |
|---|---|---|---|
| 2016/0074029 A1* | 3/2016 | O'Connell | A61B 17/02 |
| | | | 600/215 |
| 2018/0014862 A1 | 1/2018 | Raina et al. | |
| 2019/0274741 A1* | 9/2019 | Vazifehdan | A61B 17/7086 |
| 2020/0305870 A1* | 10/2020 | Shelton, IV | A61B 17/07207 |

* cited by examiner

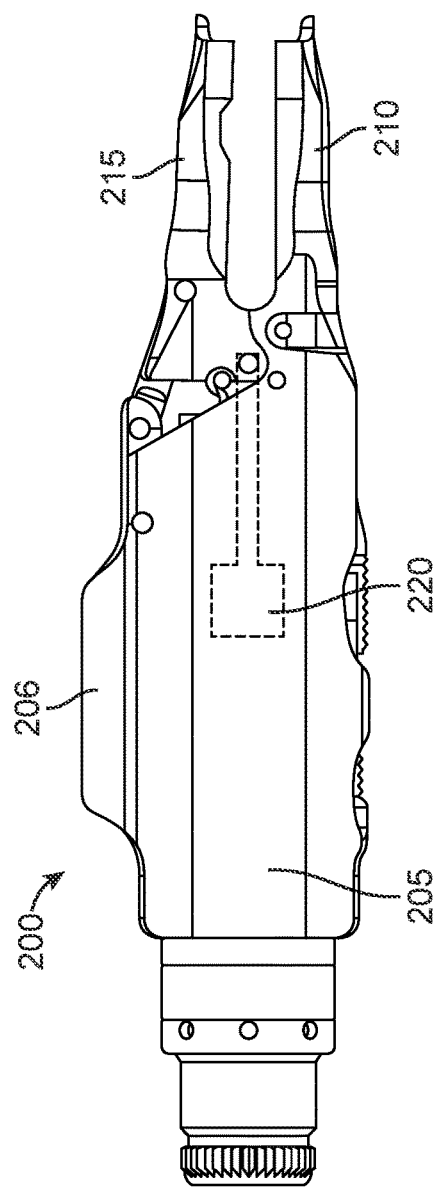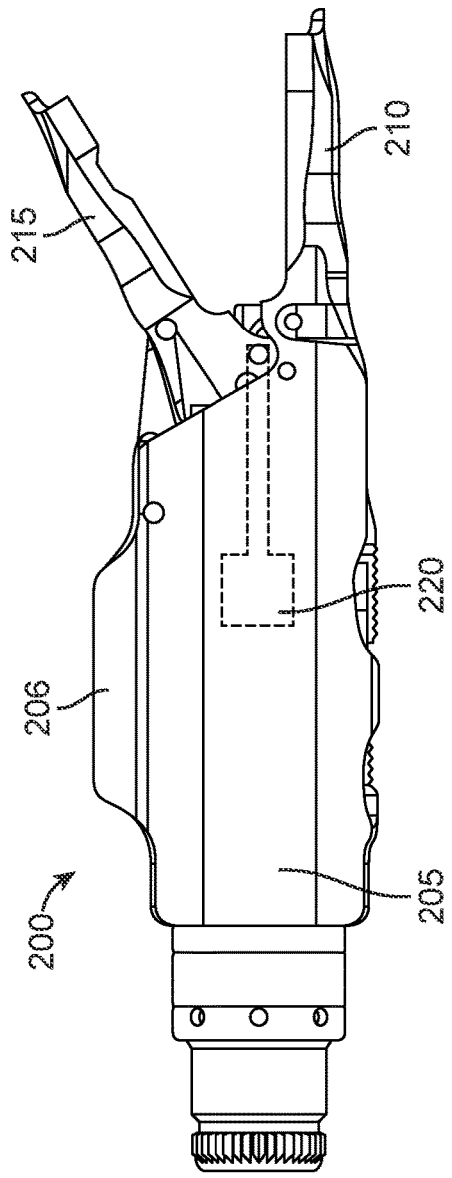

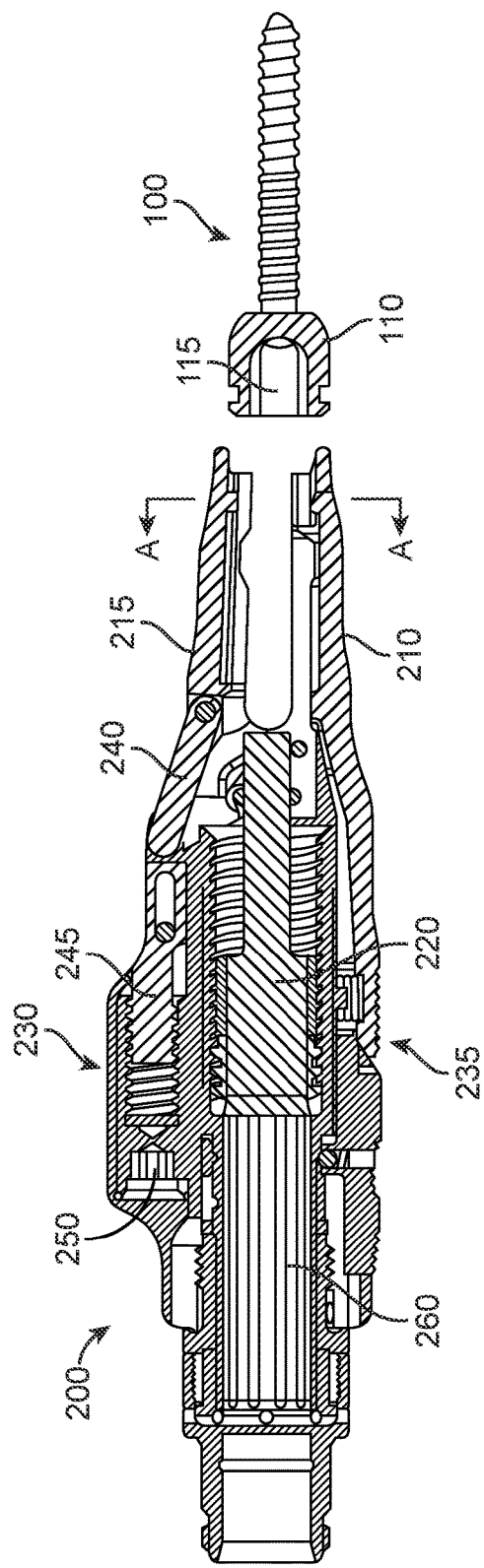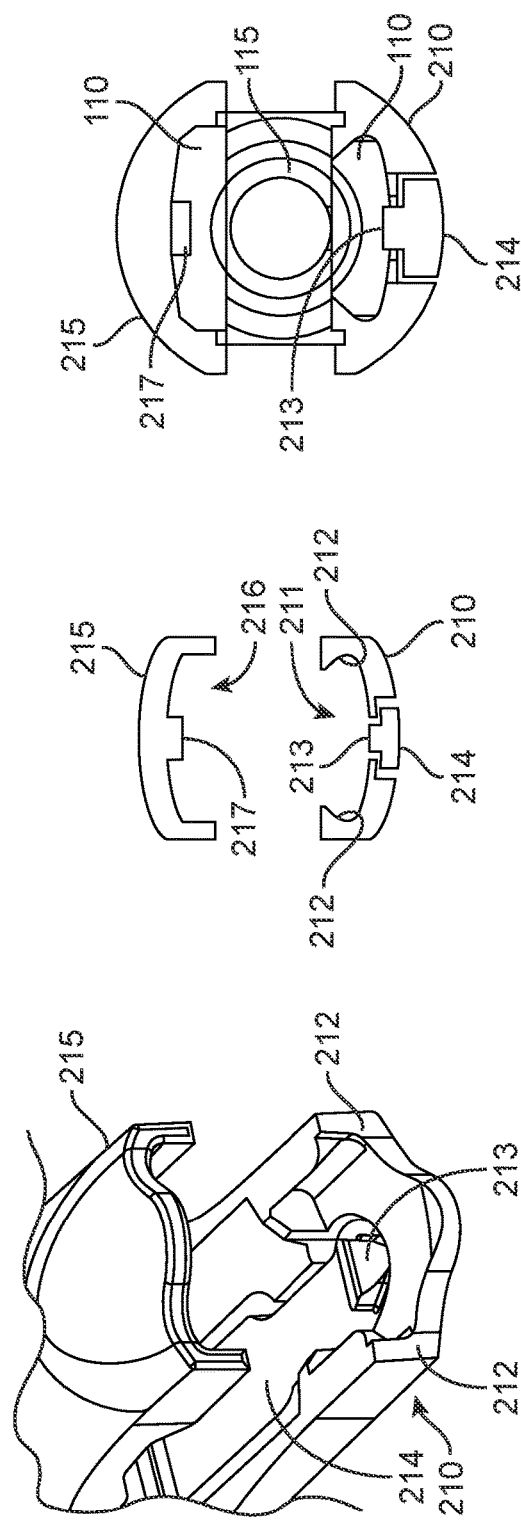

LATERAL ROD REDUCER

CROSS-REFERENCE TO RELATED APPLICATIONS

This application claims the benefit of U.S. Provisional Application No. 63/276,515 filed Nov. 5, 2021, which is incorporated herein by reference.

FIELD

The present invention relates generally to the field of surgery, and more specifically, to a lateral rod reducer for use in spinal fusion surgery.

BACKGROUND

Many spinal fixation systems use pedicle screws attached to two or more vertebrae coupled to a fixation rod. The pedicle screw includes a body member or tulip that includes a tulip slot or U-shaped channel to accept the fixation rod. A set screw is used to threadably engage the body member of the screw assembly to secure the stabilizing rod within the body member. Positioning the spinal fixation rod in the screw head typically requires the drawing of the rod to the screw using a rod reducer.

Rod reducers are placed over the spinal fixation rod and attached to the pedicle screw body member or tulip. The rod reducer then pushes the spinal fixation rod into the tulip slot or U-shaped channel and a set screw is used to clamp the rod in place.

In certain situations, the spinal fixation rod may not be aligned with the tulip slot or U-shaped channel of the pedicle screw during a spinal fusion surgery. Current rod reduction instruments do not correct misalignment of the spinal fixation rod with the tulip slot or U-shaped channel. So the surgeon must use a separate lateral reducer. Lateral reducers currently on the market utilize a hinged lever arm that, when squeezed by the surgeon, laterally reduce the rod. The lever arm concept requires that the surgeon fully squeeze and operate the lever to complete 100% of the available lateral reduction once started. The lateral reducer does not allow for incremental lateral reduction.

Thus, there is a need for an improved rod reducer that solves the problems listed above.

SUMMARY

The present invention is directed to a rod reducer that is both a lateral rod reducer and axial rod reducer. The lateral rod reducer uses an entirely different mechanism never before used for lateral reduction. The lateral rod reducer described herein is capable of both lateral reduction a spinal fixation rod and axial reduction of a spinal fixation rod. Splitting the reducer body geometry to create a jaw that is then driven by a linkage system is novel. The lateral rod reducer of the present invention allows for incremental lateral reduction that utilizes a threaded linkage feature for increased power/mechanical advantage when laterally reducing. This will allow for new techniques of lateral rod manipulation in deformity cases.

The lateral rod reducer described herein is capable of reducing a spinal fixation rod both laterally and axially to couple with a pedicle screw. The spinal fixation rod is reduced laterally with a hinged jaw to position the spinal fixation rod over the tulip slot or U-shaped channel of the pedicle screw tulip. The spinal fixation rod is then reduced axially with a ram into the U-shaped channel or tulip slot.

BRIEF DESCRIPTION OF THE DRAWINGS

FIGS. 1 and 2 show one embodiment of a lateral rod reducer.

FIG. 3 is a sectional view of the lateral rod reducer.

FIG. 4 is a perspective view showing the distal end of the fixed jaw and hinged jaw.

FIG. 5 is a sectional view at A-A of FIG. 3

FIG. 6 is a cross-sectional view showing the fixed jaw and hinge jaw coupled to the tulip of the screw.

DETAILED DESCRIPTION

Figures 7, 8, 9:
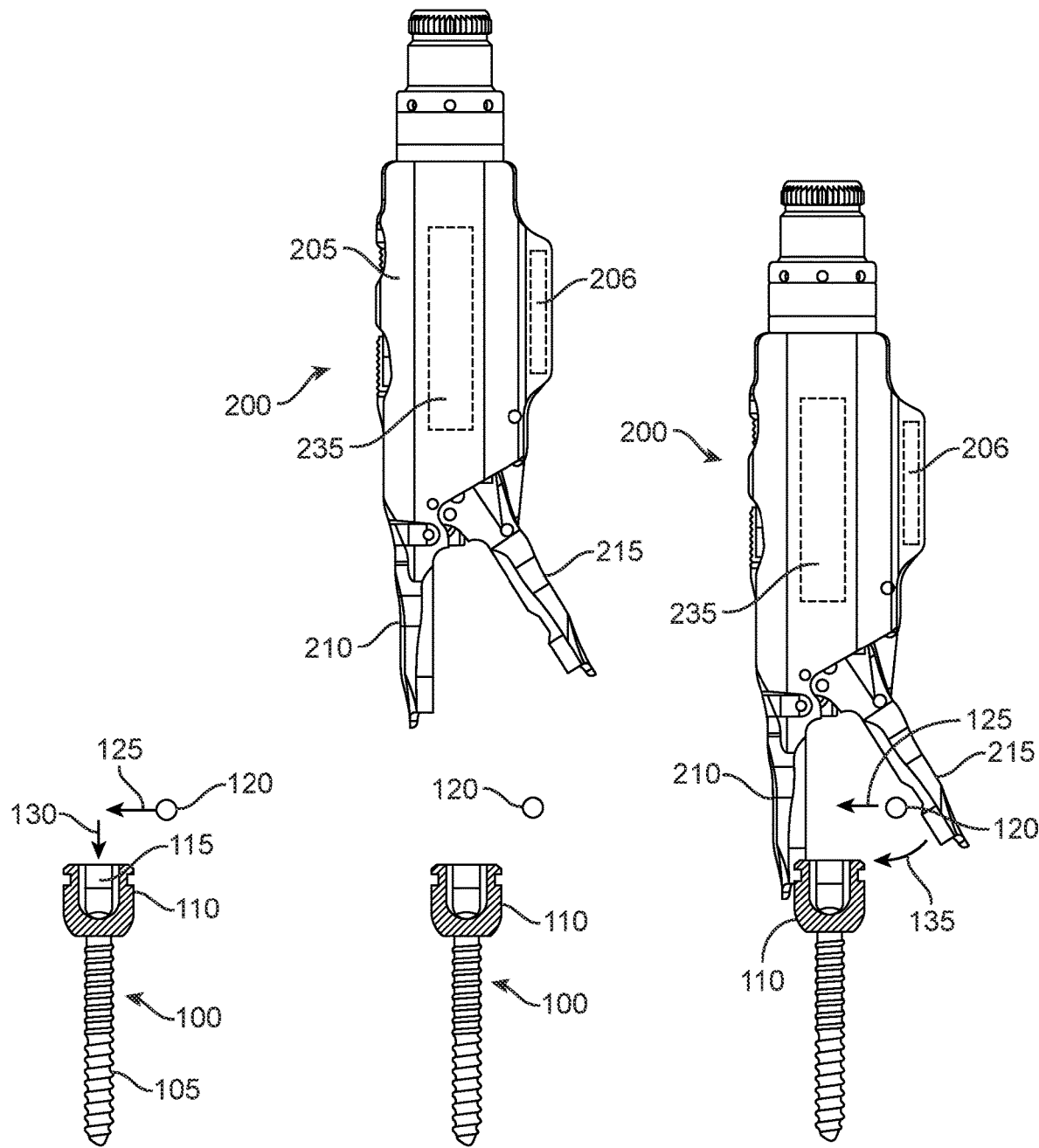
FIG. 7 is a view showing a spinal fixation rod positioned laterally from a pedicle screw.
FIGS. 8-11 are views showing operation of the lateral rod reducer moving the spinal fixation rod laterally and then moving the spinal fixation rod axially to the tulip of a pedicle screw.

In certain situations, the spinal fixation rod may not be aligned with the tulip slot or U-shaped channel of the pedicle screw during a spinal fusion surgery. The present invention solves this problem by providing a lateral rod reducer that is configured to move the spinal fixation rod that is not aligned to position it above the tulip slot or U-shaped channel of the pedicle screw. Once in position, the present invention also provides an axial rod reducer to advance the spinal fixation rod axially into the tulip slot or U-shaped channel. In some embodiments, the present invention may also advance a set screw to secure the spinal fixation rod within the tulip slot or U-shaped channel.

In the embodiments shown, the lateral rod reducer utilizes a hinged jaw coupled to a lateral reduction mechanism that is configured to extend laterally to engage a spinal fixation rod and then closes the hinged jaw to medially reduce the spinal fixation rod to the tulip slot or U-shaped channel of pedicle screw. The fixed jaw engages the pedicle screw with a dovetail connection while the hinged jaw engages the spinal fixation rod. The lateral reduction mechanism includes a threaded ram and linkage mechanism driven by a hexalobe connection at the top of the instrument. Turning the hexalobe drive closes the jaw to bring the spinal fixation rod in-line with the tulip slot. The hexalobe connection is not pertinent to the functionality, different drive patterns could be used. Once the hinged jaw is closed, the lateral rod reducer behaves like a traditional sequential reducer. Drivers are used to translate a threaded ram which pushes the rod down into the tulip slot.

FIGS. 1 and 2 show one embodiment of a lateral rod reducer 200 having a body 205 with a fixed jaw 210 and a hinged jaw 215 extending from a distal end of the body 205. The fixed jaw 210 is configured to couple with a tulip 110 of a pedicle screw 100 using a dovetail connection, and the hinged jaw 215 is configured to couple with the tulip 110. A lateral reduction mechanism 230 is configured to rotate the hinged jaw 215 laterally outward to engage a spinal fixation rod 120 and then rotate the hinged jaw 215 medially inward to reduce the spinal fixation rod 120 to the tulip 110. The axial reduction mechanism 235 with an axial threaded ram 220 is used to apply a load and reduce the spinal fixation rod 120 axially into a tulip slot 115 of the pedicle screw 100. Both the fixed jaw 210 and hinged jaw 215 are configured to engage the tulip 110 to secure the connection between the lateral rod reducer 200 and pedicle screw 100 for spinal rod reduction.

FIG. 3 is a cross-sectional view of the lateral rod reducer 200 showing the body 205 having a side lumen 206 housing the lateral reduction mechanism 230, and a central lumen 260 housing the axial reduction mechanism 235. The fixed jaw 210 is coupled to the body 205 and the hinged jaw 215 is coupled to the lateral reduction mechanism 230. In other embodiments, both the jaws may be hinged jaws. The fixed jaw 210 and hinged jaw 215 include a distal portion configured to engage the tulip or head 110 of the pedicle screw 100. The hinged jaw 215 is further configured to engage and laterally reduce a spinal fixation rod 120.

The lateral reduction mechanism 230 includes a lateral threaded ram 245 positioned within a threaded portion of the side lumen 206. A distal end of the lateral threaded ram 245 is coupled to a proximal end of a linkage mechanism 240, and a distal end of the linkage mechanism 240 is coupled to the hinged jaw 215. The lateral threaded ram 245 includes a lateral driver connection 250 at a proximal end configured to engage a lateral driver 255. The lateral driver 255 is configured to rotate the lateral threaded ram 245 to move the linkage mechanism 240 forward or backward to open or close the hinged jaw 215. The lateral driver connection 250 may be a hexalobe connection, but many different drive patterns could be used.

The axial reduction mechanism 235 includes an axial threaded ram 220 positioned within a threaded portion of the central lumen 260 of the body 205. The axial threaded ram 220 includes an axial driver connection or feature 265 at a proximal end configured to engage an axial driver 270. The axial driver 270 is configured to rotate axial threaded ram 220 to advance or retract it. The axial driver connection 265 may be a hexalobe connection, but many different drive patterns could be used. The distal end of the axial threaded ram 220 is configured to engage a spinal fixation rod 120 and reduce it to the tulip slot 115 of a pedicle screw 100. In some embodiments, the lateral driver 255 and axial driver 270 may be the same driver, so only one driver is need for lateral and axial reduction of the spinal fixation rod 120.

FIG. 4 is a perspective view showing the distal end of the fixed jaw 210 and hinged jaw 215 and FIG. 5 is a sectional view at A-A of FIG. 3 showing the engagement features of the fixed jaw 210 and hinged jaw 215.

The fixed jaw 210 has an internal pocket 211 shaped to partially wrap around the tulip's cross-sectional shape having a dovetail geometry with inwardly curved ends 212. The fixed jaw 210 is designed to slide axially on the tulip 110. This aligns the lateral rod reducer 200 with the tulip 110. The fixed jaw 210 further includes an inward protrusion 213 configured to couple with a recess in the tulip 110. The inward protrusion 213 may be part of an internal surface of the pocket 211, or may be part of a flexible attached member 214, as shown in the figures. The flexible attachment member 214 is configured to flex the inward protrusion 213 outwardly when the fixed jaw 210 is slid onto the tulip 110, then flex back when the inward protrusion 213 reaches the recess on the side of the tulip 110.

The hinged jaw 215 includes an internal pocket 216 that is U-shaped to partially wrap around the tulip's cross-sectional shape when the hinged jaw 215 is in the closed position. The hinged jaw 215 is designed to engage the tulip 110 after lateral reduction of the spinal fixation rod 120. The hinged jaw 215 includes an inward protrusion 217 configured to couple with a recess in the tulip 110.

Once the fixed jaw 210 and hinged jaw 215 are coupled to the tulip 110, the connection between the lateral rod reducer 200 and the tulip 110 of the pedicle screw 100 is secure so that they will not separate during axial reduction of the spinal fixation rod 120.

FIG. 6 is a cross-sectional view showing the fixed jaw 210 and hinge jaw 215 coupled to the tulip 110 of the screw 100. Once the fixed jaw 210 and hinged jaw 215 have coupled with the tulip 110, the lateral rod reducer 200 is locked on the screw 100 to hold it in place during axial reduction of the spinal fixation rod 120 into the tulip recess 115.

FIG. 7 is a view showing a pedicle screw 100 used in spinal surgery having threads 105 for attachment to the spine and proximal head 110 with a tulip slot or U-shaped channel 115 sized for a spinal fixation rod 120. In the figure, the spinal fixation rod 120 is positioned laterally from the pedicle screw 100 and not aligned with the tulip slot or U-shaped channel 115. In this lateral position, the spinal fixation rod 120 cannot be reduced into the tulip slot 115. The spinal fixation rod 120 will need to be moved medially 125 so that it is positioned over the tulip slot 115, then the spinal fixation rod 120 will need to be moved axially 140 into the tulip slot 115.

FIGS. 8-11 show a one embodiment of a lateral rod reducer 200 configured to laterally move 125 a spinal fixation rod 120 that is not aligned with the tulip slot or U-shaped 115 during a spinal fusion surgery to position it above the tulip slot 115. The lateral rod reducer is then configured to move the spinal fixation rod 120 axially 140 to reduce it into the tulip slot 115.

The lateral rod reducer 200 includes a body 205 housing both a lateral reduction mechanism 230 and an axial reduction mechanism. The lateral reduction mechanism includes a jaw actuation mechanism 230 coupled to fixed jaw 210 and a hinged jaw 215 extending from a distal end of the body 205. In the embodiment shown, the fixed jaw 210 is a fixed jaw and the hinged jaw 215 is a hinged jaw. In other embodiments, both the fixed and hinged jaws 210, 215 may be hinged. The lateral reduction mechanism 230 is configured to laterally translate the spinal fixation rod 120 to the pedicle screw 100. Once the fixed and hinged jaws 210, 215 are closed, the lateral rod reducer 200 utilizes a ram 225 coupled to an axial reduction mechanism 230 positioned within the body 205 to axially push or advance the spinal fixation rod 120 down into the tulip slot 115 to reduce the spinal fixation rod 120 to the pedicle screw 100. A set screw is then attached to the FIG. 8 shows the lateral rod reducer 200 approaching the pedicle screw 100 and spinal fixation rod 120. The fixed and hinged jaws 210, 215 are in the open position.

FIG. 9 shows the fixed and hinged jaws 210, 215 of the lateral rod reducer 200 in the open or expanded position with the fixed jaw 210 engaging the pedicle screw 100 and hinged jaw 215 engaging the spinal fixation rod 120. Once in position, the lateral reduction mechanism 230 rotates 135 the hinged jaw 215 toward the fixed jaw 210, which moves the spinal fixation rod 120 medially 125.

Figure 10:
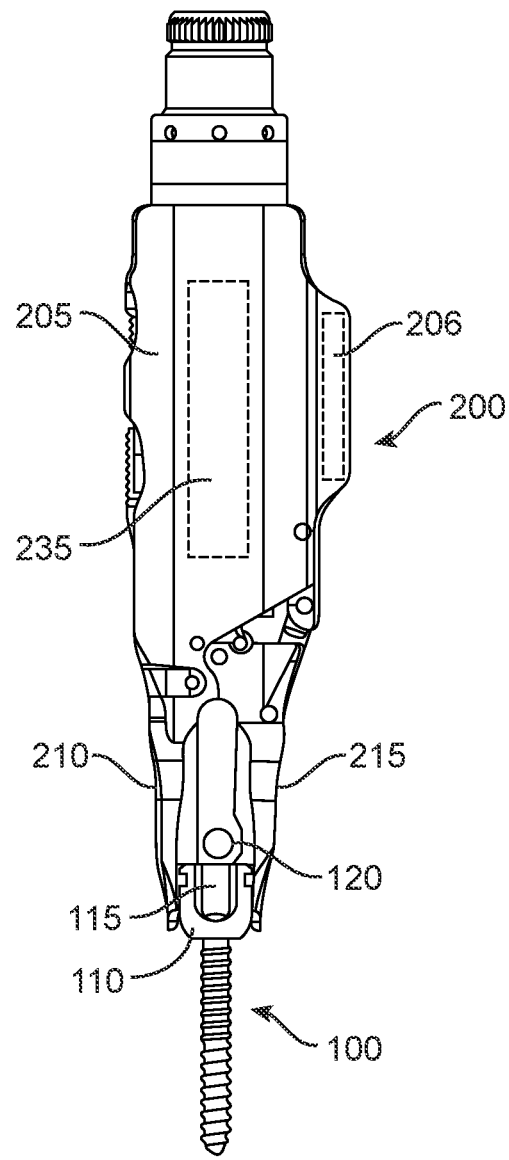

FIG. 10 shows the fixed and hinged jaws 210, 215 in the closed position engaging the head 110 of the pedicle screw 100. In this position, the spinal reduction rod 120 is above the tulip slot 115 and ready to be pushed into the tulip slot 115.

Figure 11:
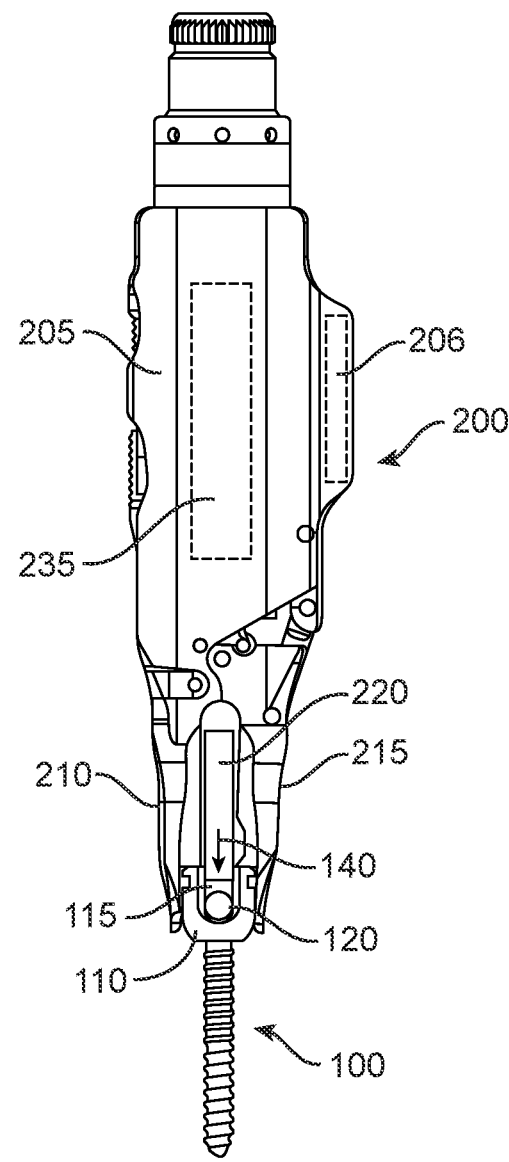

FIG. 11 shows the ram 220 extending axially 140 by the lateral reduction mechanism 230. During axial movement, the ram 220 pushes spinal fixation rod 120 into the tulip slot 115 of the pedicle screw 100.

Lateral Reduction of the Spinal Fixation Rod

In certain situations, the fixation rod 120 is not aligned with the tulip slot 115 of the pedicle screw 100 during a spinal fusion surgery. The lateral rod reducer 200 is used to reduce the spinal fixation rod with the tulip slot 115.

Figure 12:
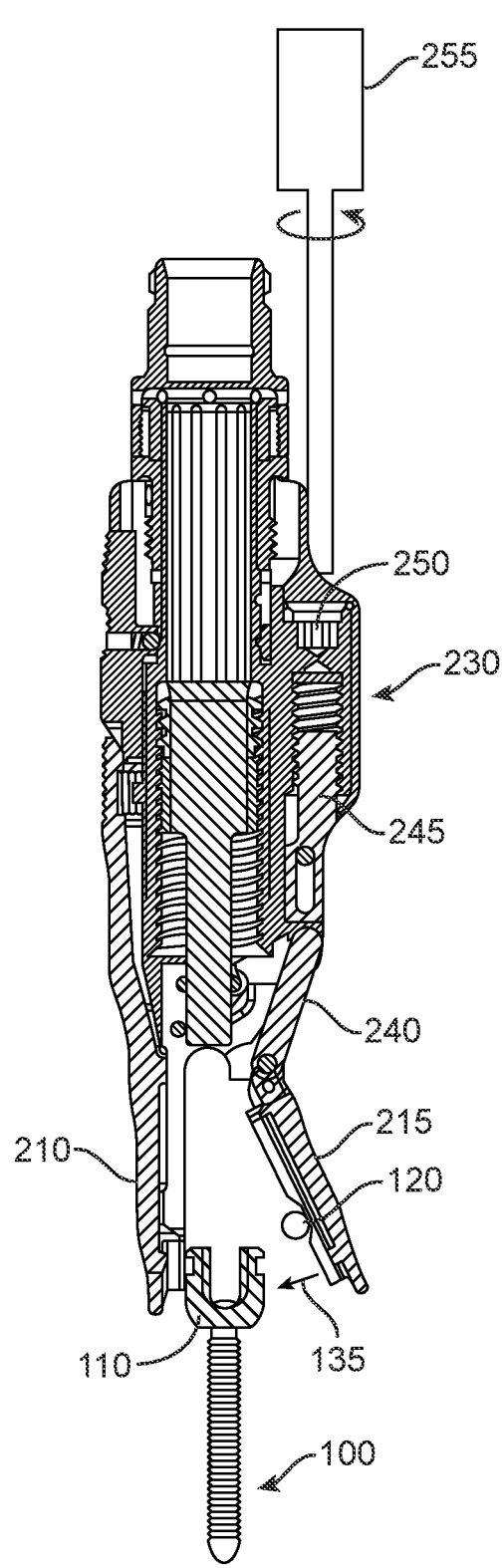
FIGS. 12 and 13 show the lateral rod reducer engaging and translating the spinal fixation rod laterally with the hinged jaw.
Figure 13:
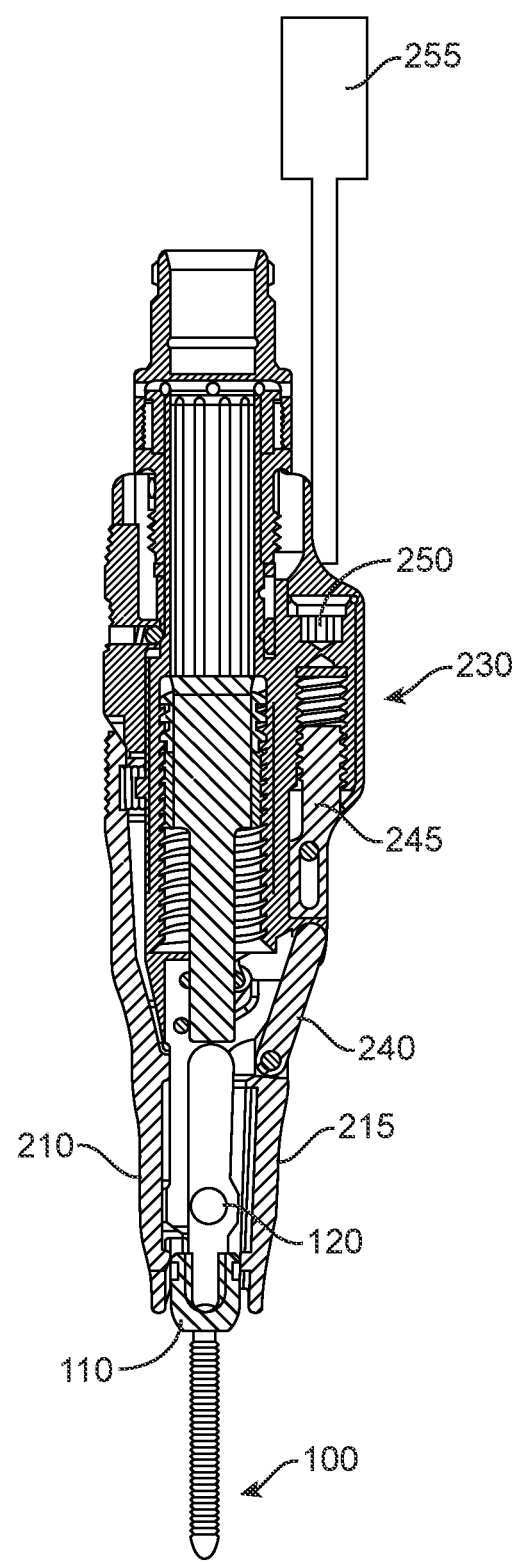

FIGS. 12 and 13 show the lateral rod reducer 200 engaging and translating the spinal fixation rod 120 laterally with the hinged jaw 215. The process starts with the hinged jaw 215 in the open position, with the fixed jaw 210 engaging the tulip 110 and hinged jaw 215 engaging the spinal fixation rod 120 (FIG. 12). The surgeon uses the lateral driver 255 to rotate the hexalobe connection 250 to drive the lateral threaded ram 245 and linkage mechanism 240, which rotates the hinged jaw 215 medially from the open position to the closed position, where the spinal reduction rod 120 is above the tulip slot 115 and ready to be pushed into the tulip slot 115 (FIG. 13). In the closed position, the hinged jaw 215 engages the tulip 110. The fixed jaw 210 and hinge jaw 215 may include engagement features to couple with the tulip 110 and lock the lateral rod reducer 200 to the screw 100 to assist in axial reduction of the spinal fixation rod. 120

Axial Reduction of the Spinal Fixaiton Rod

Once the hinged jaw 215 is closed, the lateral rod reducer 200 behaves like a traditional sequential reducer. An axial drive 270 is use to translate a threaded ram 220 axially, which reduces the spinal fixation rod 120 into the tulip slot 115.

Figure 14:
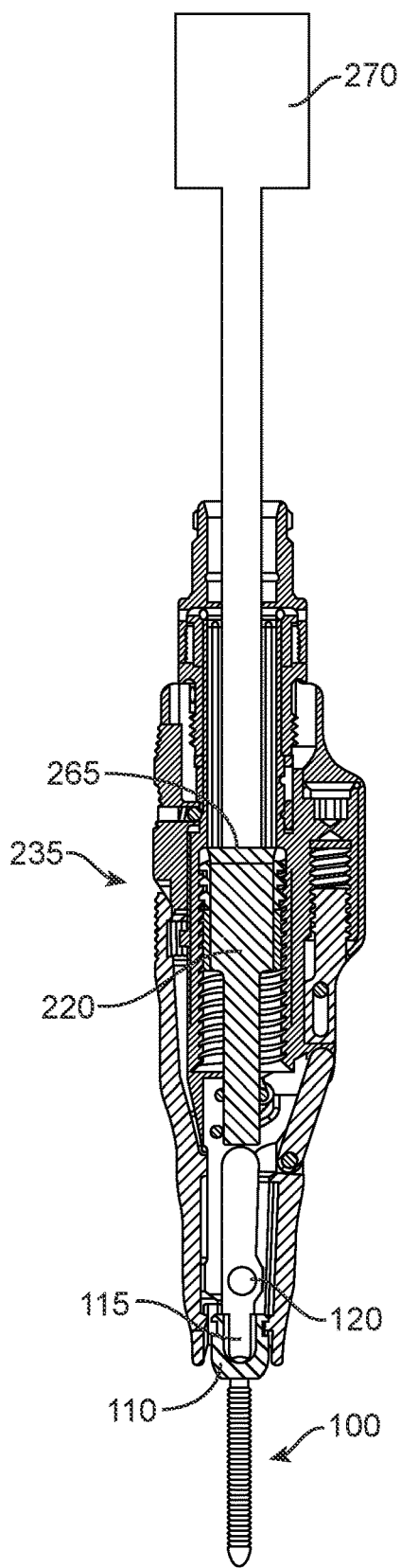
FIGS. 14 and 15 show axial reduction of the spinal fixation rod into the tulip slot.
Figure 15:
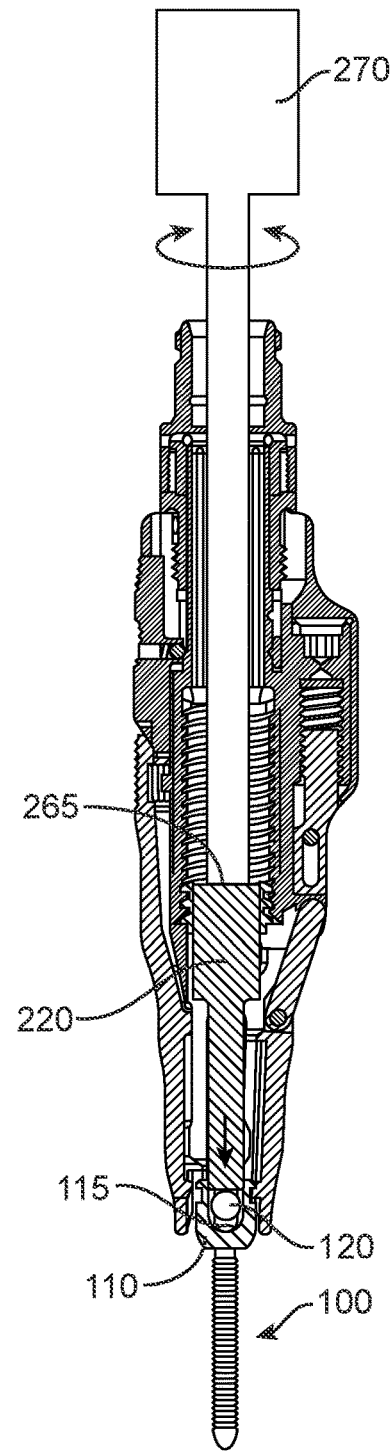

FIGS. 14 and 15 show axial reduction of the spinal fixation rod 120 into the tulip slot 115. The fixed jaw 210 and hinged jaw 215 are coupled to the tulip 110. The axial driver 270 engages the proximal end of the axial threaded ram 220. As the axial driver 270 is rotated, the axial threaded ram 220 advances distally and engages the spinal fixation rod 120 and pushes it distally into the tulip slot 115. Once the spinal fixation rod 120 is within the tulip slot 115, a set screw is used to lock them together.

The lateral rod reducer 200 is then removed.

Example embodiments of the methods and systems of the present invention have been described herein. As noted elsewhere, these example embodiments have been described for illustrative purposes only and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents.

The invention claimed is:

1. A lateral rod reducer comprising:
    a body having a central lumen and a side lumen;
    an axial reduction mechanism with an axial threaded ram positioned within the central lumen of the body;
    a lateral reduction mechanism with a lateral threaded ram positioned within the side lumen of the body;
    a linkage mechanism having a proximal end coupled to a distal end of the lateral threaded ram;
    a fixed jaw extending from a distal end of the body, the fixed jaw being configured to couple with the tulip of a pedicle screw; and
    a hinged jaw pivotably coupled to a distal end of the linkage mechanism;
    wherein rotation of the lateral threaded ram moves the linkage mechanism forward or backward to rotate the hinged jaw to an open position, and rotate the hinged jaw to a closed position, the hinged jaw being configured to engage a spinal fixation rod in the open position and medially reduce the spinal fixation rod to the tulip in the closed position, the hinged jaw further configured to couple with the tulip in the closed position;
    wherein the axial threaded ram being configured to extend axially from the central lumen of the body and apply a force to reduce the spinal fixation rod to a tulip slot in the tulip.

2. The lateral rod reducer of claim 1, wherein the lateral threaded ram is positioned within a threaded portion of the side lumen, the lateral threaded ram having a driver connection at a proximal end configured to engage a lateral driver.

3. The lateral rod reducer of claim 1, wherein the fixed jaw couples with the tulip using a dovetail connection.

4. The lateral rod reducer of claim 3, wherein the fixed jaw includes dovetail geometry for the dovetail connection having an internal pocket with inwardly curved ends shaped to partially wrap around the tulip's cross-sectional shape.

5. The lateral rod reducer of claim 1, wherein the axial threaded ram is positioned within a threaded portion of the central lumen and includes a driver connection at a proximal end configured to engage an axial driver, and rotation of the axial threaded ram moves the axial threaded ram axially forward or backward.

6. A lateral rod reducer comprising:
    a body;
    a fixed jaw extending from a distal end of the body, the fixed jaw being configured to couple with a tulip of a pedicle screw;
    a hinged jaw extending from a distal end of the body;
    a linkage mechanism having a distal end pivotably coupled to the hinged jaw; and
    a lateral reduction mechanism with
      a lateral threaded ram positioned within a side lumen of the body,
      the linkage mechanism having a proximal end coupled to the distal end of the lateral threaded ram;
      wherein rotation of the lateral threaded ram moves the linkage mechanism forward or backward to rotate the hinged jaw between an open or closed position;
      wherein the hinged jaw is configured to engage a spinal fixation rod in the open position and medially reduce the spinal fixation rod to the tulip in the closed position; and
    an axial reduction mechanism with an axial threaded ram positioned within a threaded portion of a central lumen of the body and rotation of the axial threaded ram within the threaded portion lumen moves the axial threaded ram forward or backward axially and to extend axially from the body and apply a load to reduce the spinal fixation rod to a tulip slot in the tulip.

7. The lateral rod reducer of claim 6, wherein the lateral threaded ram is positioned within a threaded portion of the side lumen and includes a driver connection at a proximal end configured to engage a lateral driver.

8. The lateral rod reducer of claim 6, wherein the fixed jaw couples with the tulip using a dovetail connection.

9. The lateral rod reducer of claim 8, wherein the fixed jaw includes dovetail geometry for the dovetail connection having an internal pocket with inwardly curved ends shaped to partially wrap around the tulip's cross-sectional shape.

10. A lateral rod reducer comprising:
a body having a central lumen and a side lumen;
an axial reduction mechanism positioned within the central lumen of the body configured to apply an axial force to reduce a spinal fixation rod into a tulip slot of pedicle screw;
a lateral reduction mechanism positioned within the side lumen of the body configured to apply a lateral force to reduce a spinal fixation rod to the tulip slot of the pedicle screw, the lateral reduction mechanism having:
a lateral threaded ram positioned within a threaded portion of the side lumen;
a linkage mechanism having a proximal end coupled to a distal end of the lateral reduction mechanism;
a fixed jaw extending from a distal end of the body; and
a hinged jaw pivotably coupled to the distal end of the linkage mechanism;
wherein rotation of the lateral threaded ram is configured to move the linkage mechanism backward to rotate the hinged jaw outward to engage a spinal fixation rod in an open position, then move the linkage mechanism forward to rotate the hinged jaw inward and apply a lateral force to reduce the spinal fixation rod to the tulip in the closed position, the hinged jaw further configured to couple with the tulip in the closed position;
wherein the axial threaded ram being configured to apply the axial force to reduce the spinal fixation rod to a tulip slot in the tulip.

11. The lateral rod reducer of claim 10, wherein the lateral threaded ram includes a driver connection at a proximal end configured to engage a lateral driver.

12. The lateral rod reducer of claim 10, wherein the fixed jaw couples with the tulip using a dovetail connection.

13. The lateral rod reducer of claim 12, wherein the fixed jaw includes dovetail geometry for the dovetail connection having an internal pocket with inwardly curved ends shaped to partially wrap around the tulip's cross-sectional shape.

14. The lateral rod reducer of claim 10, wherein the axial threaded ram includes a driver connection at a proximal end configured to engage an axial driver.

* * * * *